US008809411B2

(12) United States Patent
Rooijmans

(10) Patent No.: US 8,809,411 B2
(45) Date of Patent: *Aug. 19, 2014

(54) HYDROPHILIC COATING

(75) Inventor: Marnix Rooijmans, Born (NL)

(73) Assignee: DSM IP Assets B.V., Heerlen (NL)

( * ) Notice: Subject to any disclaimer, the term of this patent is extended or adjusted under 35 U.S.C. 154(b) by 537 days.

This patent is subject to a terminal disclaimer.

(21) Appl. No.: 12/528,102

(22) PCT Filed: Feb. 27, 2008

(86) PCT No.: PCT/EP2008/052396
§ 371 (c)(1),
(2), (4) Date: Nov. 5, 2010

(87) PCT Pub. No.: WO2008/104572
PCT Pub. Date: Sep. 4, 2008

(65) Prior Publication Data
US 2011/0046255 A1 Feb. 24, 2011

Related U.S. Application Data

(60) Provisional application No. 60/907,607, filed on Apr. 11, 2007.

(30) Foreign Application Priority Data

Feb. 28, 2007 (EP) .................................. 07004101

(51) Int. Cl.
G03G 9/097 (2006.01)
C08B 37/00 (2006.01)
G03F 7/031 (2006.01)
C08F 2/50 (2006.01)
C08F 2/46 (2006.01)
B29C 71/04 (2006.01)
A61L 2/08 (2006.01)
A61L 24/00 (2006.01)
C08G 61/04 (2006.01)

(52) U.S. Cl.
USPC ............ 522/11; 522/7; 522/8; 522/6; 522/68; 522/1; 522/71; 522/189; 522/184; 520/1

(58) Field of Classification Search
USPC ......... 522/8–10, 86, 109–112, 11, 7, 6, 68, 1, 522/71, 189, 184; 520/1
See application file for complete search history.

(56) References Cited

U.S. PATENT DOCUMENTS

| 4,105,519 A | 8/1978 | Pennewiss et al. |
| 4,111,922 A | 9/1978 | Beede et al. |
| 4,117,184 A | 9/1978 | Erickson et al. |
| 4,272,620 A | 6/1981 | Ichimura |
| 4,612,336 A | 9/1986 | Yada et al. |
| 4,818,325 A | 4/1989 | Hiraiwa et al. |
| 4,874,822 A | 10/1989 | Rasmussen et al. |
| 4,876,126 A | 10/1989 | Takemura et al. |
| 5,005,287 A | 4/1991 | Ritter |
| 5,008,301 A | 4/1991 | Dennis et al. |
| 5,077,352 A | 12/1991 | Elton |
| 5,084,315 A | 1/1992 | Karimi et al. |
| 5,091,205 A | 2/1992 | Fan |
| 5,135,516 A | 8/1992 | Sahatjian et al. |
| 5,317,063 A | 5/1994 | Komatsu et al. |
| 5,670,557 A | 9/1997 | Dietz |
| 5,700,559 A | 12/1997 | Sheu et al. |
| 5,702,754 A | 12/1997 | Zhong |
| 5,756,144 A | 5/1998 | Wolff et al. |
| 5,804,318 A | 9/1998 | Pinchuk et al. |
| 5,985,990 A | 11/1999 | Kantner et al. |
| 5,994,419 A | 11/1999 | Collette et al. |
| 6,048,620 A | 4/2000 | Zhong |
| 6,110,451 A | 8/2000 | Matz et al. |
| 6,120,904 A | 9/2000 | Hostettler et al. |
| 6,221,425 B1 | 4/2001 | Michal et al. |
| 6,238,799 B1 * | 5/2001 | Opolski ..................... 428/423.1 |
| 6,310,116 B1 | 10/2001 | Yasuda et al. |
| 6,565,981 B1 | 5/2003 | Messner et al. |
| 6,589,665 B2 | 7/2003 | Chabrecek et al. |
| 6,673,053 B2 | 1/2004 | Wang et al. |
| 6,709,706 B2 | 3/2004 | Zhong et al. |
| 6,720,130 B1 | 4/2004 | Zhong et al. |
| 6,835,783 B1 | 12/2004 | Gartner et al. |
| 6,849,685 B2 | 2/2005 | Soerens et al. |
| 6,887,961 B2 | 5/2005 | Soerens et al. |

(Continued)

FOREIGN PATENT DOCUMENTS

| EP | 0 289 996 | 11/1988 |
| EP | 0 405 464 | 1/1991 |

(Continued)

OTHER PUBLICATIONS

International Search Report for PCT/EP2008/052396 mailed Feb. 16, 2009.
Written Opinion for PCT/EP2008/052396 mailed Feb. 16, 2009.
Alt, V. et al., "Plasma Polymer Coating with High-Porosity Silver for Antimicrobial Protection of Osteosynthetic Devices", Osteosynthese International 2005—Kongress, Oral Presentation, No. 075, Sep. 15, 2005, 1 page.
Asha, S. K. et al., "Synthesis and Curing Studies of PPG Based Telechelic Urethane Methacrylic Macromonomers", European Polymer Journal, vol. 41, No. 1, Jan. 2005, pp. 23-33.
Guggenbichler, J.P. et al., "A New Technology of Microdispersed Silver in Polyurethane Induces Antimicrobial Activity in Central Venous Catheters", Infection, vol. 27, Suppl. 1, pp. S16-S23, 1999.

(Continued)

Primary Examiner — Ling Choi
Assistant Examiner — Jessica E Whiteley
(74) Attorney, Agent, or Firm — Nixon & Vanderhye P.C.

(57) ABSTRACT

The invention relates to a coating formulation for preparing a hydrophilic coating, wherein the hydrophilic coating formulation comprises a hydrophilic polymer, a supporting polymer comprising a backbone and at least 2 reactive moieties capable of undergoing polymerization reactions, a Norrish Type I photoinitiator and a Norrish Type II photoinitiator.

19 Claims, No Drawings

(56) References Cited

U.S. PATENT DOCUMENTS

| | | |
|---|---|---|
| 7,264,859 B2 | 9/2007 | Rouns et al. |
| 7,544,381 B2 | 6/2009 | Kangas |
| 2001/0011165 A1 | 8/2001 | Engelson et al. |
| 2001/0027299 A1 | 10/2001 | Yang et al. |
| 2002/0002353 A1* | 1/2002 | Michal et al. ............... 604/265 |
| 2002/0013549 A1 | 1/2002 | Zhong et al. |
| 2003/0013615 A1 | 1/2003 | Levy |
| 2003/0096131 A1 | 5/2003 | Beavers et al. |
| 2004/0019168 A1 | 1/2004 | Soerens et al. |
| 2004/0043688 A1 | 3/2004 | Soerens et al. |
| 2004/0110861 A1 | 6/2004 | Shorbu et al. |
| 2004/0135967 A1* | 7/2004 | Carney et al. ............... 351/159 |
| 2004/0143180 A1 | 7/2004 | Zhong et al. |
| 2005/0054774 A1 | 3/2005 | Kangas |
| 2005/0080157 A1 | 4/2005 | Wagener et al. |
| 2005/0100580 A1 | 5/2005 | Osborne et al. |
| 2005/0170071 A1* | 8/2005 | Eramo ............... 427/2.1 |
| 2005/0191430 A1 | 9/2005 | Rubner et al. |
| 2006/0240060 A1* | 10/2006 | Bavaro ............... 424/422 |
| 2007/0167735 A1 | 7/2007 | Zhong et al. |
| 2008/0292776 A1 | 11/2008 | Dias et al. |
| 2008/0306455 A1 | 12/2008 | Dias et al. |
| 2009/0169715 A1 | 7/2009 | Dias et al. |
| 2010/0113871 A1 | 5/2010 | Dias et al. |
| 2010/0198168 A1 | 8/2010 | Rooijmans |
| 2011/0059874 A1 | 3/2011 | Rooijmans et al. |

FOREIGN PATENT DOCUMENTS

| | | |
|---|---|---|
| EP | 0 480 809 | 4/1992 |
| EP | 1 065 738 | 1/2001 |
| EP | 1 621 217 | 2/2006 |
| EP | 1 776 968 | 4/2007 |
| JP | 54-147696 | 11/1979 |
| JP | 04-144567 | 5/1992 |
| JP | 5-300940 | 11/1993 |
| JP | 06-039347 | 2/1994 |
| JP | 10-211273 | 8/1998 |
| JP | 10-277144 | 10/1998 |
| JP | 11-172149 | 6/1999 |
| JP | 2001-000531 | 1/2001 |
| JP | 2007-23130 | 2/2007 |
| WO | 93/11751 | 6/1993 |
| WO | 96/28762 | 9/1996 |
| WO | WO 97/17378 | 5/1997 |
| WO | 97/29160 | 8/1997 |
| WO | 98/50461 | 11/1998 |
| WO | 98/58989 | 12/1998 |
| WO | WO 99/38546 | 8/1999 |
| WO | WO 01/51103 | 7/2001 |
| WO | WO 01/92584 | 12/2001 |
| WO | 2004/056909 | 7/2004 |
| WO | WO 2004/060427 | 7/2004 |
| WO | 2004/091685 | 10/2004 |
| WO | 2006/042514 | 4/2006 |
| WO | WO 2006/056482 | 6/2006 |
| WO | 2007/065722 | 6/2007 |
| WO | WO 2008/012325 | 1/2008 |
| WO | 2008/031596 | 3/2008 |
| WO | WO 2008/071796 | 6/2008 |
| WO | 2008/104573 | 8/2008 |
| WO | WO 2011/157805 | 12/2011 |

OTHER PUBLICATIONS

Samuel, U. et al., "Prevention of Catheter-Related Infections: the Potential of a New Nano-Silver Impregnated Catheter", International Journal of Antimicrobial Agents, vol. 23, Suppl. 1, pp. S75-S78, Mar. 2004.
Database WPI Week 199517, *Thomas Scientific*, XP002451204 & JP 07 053895, Feb. 28, 1995 Abstract.
International Search Report for PCT/EP2006/011903 dated Aug. 8, 2007.
Written Opinion of the International Searching Authority for PCT/EP2006/011903 dated Aug. 8, 2007.
International Search Report for PCT/EP2006/011904 mailed Mar. 16, 2007.
Written Opinion of the International Searching Authority for PCT/EP2006/011904 mailed Mar. 16, 2007.
International Search Report for PCT/EP2007/007995 mailed Feb. 27, 2008.
Written Opinion of the International Searching Authority for PCT/EP2007/007995 mailed Feb. 27, 2008.
International Search Report for PCT/EP2008/052397 mailed Jan. 13, 2009.
International Search Report for PCT/EP2009/052918 mailed Jun. 22, 2009.
Written Opinion of the International Searching Authority for PCT/EP2009/052918 mailed Jun. 22, 2009.
International Search Report for PCT/EP2006/011902, dated Aug. 6, 2007.
Written Opinion of the International Searching Authority for PCT/EP2006/011902, dated Aug. 6, 2007.
International Search Report for PCT/EP2007/007984, dated Apr. 11, 2008.
Written Opinion of the International Searching Authority for PCT/EP2007/007984, dated Apr. 11, 2008.
International Search Report for PCT/EP2011/060066, mailed Sep. 5, 2011.
Written Opinion of the International Searching Authority for PCT/EP2011/060066, mailed Sep. 5, 2011.
Japanese Patent Office, Notice of Reasons for Rejection, P2008-343747, Dispatch No. 004257 (Jan. 10, 2012) (English Translation).
Japanese Patent Office, Final Rejection, P2008-543747, Dispatch No. 472881 (Jul. 17, 2012) (English Translation).
U.S. Appl. No. 13/704,714, filed Dec. 17, 2012.
JP Office Action with English-Language Translation mailed Dec. 18, 2012, (Appln No. P2009-551200).
JP Office Action with English-Language Translation mailed Dec. 18, 2013, (Appln No. P2009-551201).

* cited by examiner

HYDROPHILIC COATING

This application is the U.S. national phase of International Application No. PCT/EP2008/052396 filed 27 Feb. 2008 which designated the U.S. and claims priority to European Patent Application No. 07004101.7 filed 28 Feb. 2007 and U.S. Provisional Application No. 60/907,607 filed 11 Apr. 2007, the entire contents of each of which are hereby incorporated by reference.

This invention relates to a coating formulation for preparing a hydrophilic coating. The invention further relates to a coating system, a hydrophilic coating, a lubricious coating, use of a Norrish Type I and a Norrish Type II photoinitiator in a lubricious coating, an article, a medical device or component and a method of forming a hydrophilic coating on a substrate.

Many medical devices, such as guide wires, urinary and cardiovascular catheters, syringes, and membranes need to have a lubricant applied to the outer and/or inner surface to facilitate insertion into and removal from the body and/or to facilitate drainage of fluids from the body. Lubricious properties are also required so as to minimize soft tissue damage upon insertion or removal. Especially, for lubrication purposes, such medical devices may have a hydrophilic surface coating or layer which becomes lubricious and attains low-friction properties upon wetting, i.e. applying a wetting fluid for a certain time period prior to insertion of the device into the body of a patient. A coating or layer which becomes lubricious after wetting is hereinafter referred to as a hydrophilic coating. A coating obtained after wetting is hereinafter referred to as a lubricious coating.

It has now been observed that such lubricious coatings are often prone to wear and as such may lose their lubricious properties upon use.

Therefore it is an object of the present invention to provide a lubricious coating that exhibits an improved wear resistance in addition to a high lubricity.

Surprisingly it has now been found that a lubricious coating with an improved wear resistance can be obtained by using a coating formulation for preparing a hydrophilic coating, wherein the hydrophilic coating formulation comprises:
  (a) a hydrophilic polymer.
  (b) a supporting polymer comprising a backbone and at least 2 reactive moieties capable of undergoing polymerization reactions, wherein the supporting polymer has a number average molecular weight in the range 750-20,000 g/mol, preferably 1,000-15,000 g/mol, more preferably 1,100-10,000 g/mol, in particular 1,200-7,000, more in particular 1,400-5,000 g/mol;
  (c) a Norrish Type I photoinitiator; and
  (d) a Norrish Type II photoinitiator.

It has further been found that the hydrophilic coatings obtainable by curing the hydrophilic coating formulation according to the invention are extremely wear resistant in tortuous tests compared to similar coatings known in the art. As a consequence the lubricity of the hydrophilic coatings is preserved despite repetitive rubs in the gauze rub test, which is described in the experimental section. This is particularly advantageous for cardiovascular applications such as guide wires and catheters, in which the hydrophilic coating experiences serious torture.

Within the context of the invention "lubricious" is defined as having a slippery surface. A coating on the outer or inner surface of a medical device, such as a catheter, is considered lubricious if (when wetted) it can be inserted into the intended body part without leading to injuries and/or causing unacceptable levels of discomfort to the subject. In particular, a coating is considered lubricious if it has a friction as measured on a Harland FTS5000 Friction Tester (HFT) of 20 g or less, preferably of 15 g or less, at a clamp-force of 300 g, a pull speed of 1 cm/s, and a temperature of 22° C. The protocol is as indicated in the Examples.

The term "wetted" is generally known in the art and—in a broad sense—means "containing water". In particular the term is used herein to describe a coating that contains sufficient water to be lubricious. In terms of the water concentration, usually a wetted coating contains at least 10 wt % of water, based on the dry weight of the coating, preferably at least 50 wt %, based on the dry weight of the coating, more preferably at least 100 wt % based on the dry weight of the coating. For instance, in a particular embodiment of the invention a water uptake of about 300-500 wt % water is feasible. Examples of wetting fluids are treated or untreated water, water-containing mixtures with for example organic solvents or aqueous solutions comprising for example salts, proteins or polysaccharides. In particular a wetting fluid can be a body fluid.

The Norrish Type I and Norrish Type II photoinitiators are used to cure the hydrophilic coating formulation according to the invention, for example using visible light or UV, electro-beam, or gamma radiation to form the hydrophilic coating. Herein both Norrish Type I and Norrish Type II photoinitiators are free-radical photoinitiators, but are distinguished by the process by which the initiating radicals are formed. Compounds that undergo unimolecular bond cleavage of the chromophore upon irradiation to generate radicals that initiate polymerization are termed Norrish Type I or homolytic photoinitiators. A Norrish Type II photoinitiator generates radicals indirectly by hydrogen abstraction from a suitable synergist, which may be a low molecular weight compound or a polymer.

Compounds that undergo unimolecular bond cleavage upon irradiation are termed Norrish Type I or homolytic photoinitiators, as shown by formula (1):

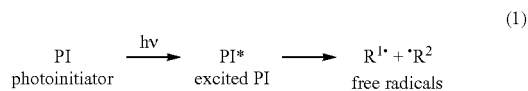

(1)

Depending on the nature of the functional group and its location in the molecule relative to the carbonyl group, the fragmentation can take place at a bond adjacent to the carbonyl group (α-cleavage), at a bond in the β-position (β-cleavage) or, in the case of particularly weak bonds (like C—S bonds or O—O bonds), elsewhere at a remote position. The most important fragmentation in photoinitiator molecules is the α-cleavage of the carbon-carbon bond between the carbonyl group and the alkyl residue in alkyl aryl ketones, which is known as the Norrish Type I reaction.

If the photoinitiator, while being in the excited state, interacts with a second molecule (a coinitiator COI) to generate radicals in a bimolecular reaction as shown by formula (2), the photoinitiator is termed a Norrish Type II photoinitiator. In general, the two main reaction pathways for Norrish Type II photoinitiators are hydrogen abstraction by the excited initiator or photoinduced electron transfer, followed by fragmentation. Hydrogen abstraction is a typical reaction of excited diaryl ketones. Photoinduced electron transfer is a more general process, which is not limited to a certain class of compounds.

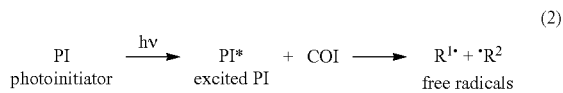

(2)

Examples of suitable Norrish Type I or free-radical photoinitiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Commercial examples of suitable Norrish Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly {2-hydroxy-2-methyl-1-[4-(1-methylvinyl)phenyl]propan-1-one}, Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethyl-benzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), and the like. Also mixtures of type I photoinitiators can be used.

Examples of Norrish Type II photoinitiators that can be used in the hydrophilic coating formulation according to the invention include aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photoinitiators.

Preferred are Norrish Type I and Norrish Type II photoinitiators which are water-soluble or can be adjusted to become water-soluble, also preferred photoinitiators are polymeric or polymerisable photoinitiators.

Generally the total amount of photoinitiator in the hydrophilic coating formulation is between 0.2 and 10 wt %, preferably between 0.8 and 8 wt % based on the total weight of the dry coating.

Hereinafter all percentages of components given in the application are based on the total weight of the dry coating. i.e. the hydrophilic coating formed upon curing the hydrophilic coating formulation.

Typically the weight ratio Norrish Type I photoinitiator: Norrish Type II photoinitiator is between 10:1 and 1:10, preferably between 5:1 and 1:5.

WO2006/056482 discloses a process for providing medical devices with lubricious coatings, wherein a Norrish I type photoinitiator is used to induce crosslinks between two polymers.

US2006/024060 discloses hydrophilic lubricious polymer blends of polyethylene oxide and polyether block amide with an improved resistance to being physically abraded from a surface.

In none of the above patent applications the simultaneous use of a Norrish Type I and a Norrish Type II photoinitiator is disclosed.

The coating formulation according to the invention also comprises a hydrophilic polymer.

Within the context of the invention the term polymer is used for a molecule comprising two or more repeating units. In particular it may be composed of two or more monomers which may be the same or different. As used herein, the term includes oligomers and prepolymers. Usually polymers have a number average weight ($M_n$) of about 500 g/mol or more, in particular of about 1000 g/mol or more, although the $M_n$ may be lower in case the polymer is composed of relatively small monomeric units. Herein and hereinafter the $M_n$ is defined as the $M_n$ as determined by light scattering, optionally in combination with Size Exclusion Chromatography (SEC).

A hydrophilic polymer is understood to be a high molecular weight linear, branched or crosslinked polymer composed of macromolecules comprising constitutional units. The hydrophilic polymer is capable of providing hydrophilicity to a coating and may be synthetic or bio-derived and can be blends or copolymers of both. The hydrophilic polymer may be non-ionic or ionic. In the hydrophilic coating formulation one or more non-ionic or ionic hydrophilic polymers may be applied, or a combination of one or more non-ionic and ionic hydrophilic polymers.

Non-ionic hydrophilic polymers include but are not limited to poly(lactams), for example polyvinylpyrollidone (PVP), polyurethanes, homo- and copolymers of acrylic and methacrylic acid, polyvinyl alcohol, polyvinylethers, maleic anhydride based copolymers, polyesters, vinylamines, polyethyleneimines, polyethyleneoxides, polypropyleneoxides, poly (carboxylic acids), polyamides, polyanhydrides, polyphosphazenes, cellulosics, for example methyl cellulose, carboxymethyl cellulose, hydroxymethyl cellulose, and hydroxypropylcellulose, heparin, dextran, polypeptides, for example collagens, fibrins, and elastin, polysaccharides, for example chitosan, hyaluronic acid, alginates, gelatin, and chitin, polyesters, for example polylactides, polyglycolides, and polycaprolactones, polypeptides, for example collagen, albumin, oligo peptides, polypeptides, short chain peptides, proteins, and oligonucleotides.

Generally the non-ionic hydrophilic polymer has a molecular weight in the range of about 8,000 to about 5,000,000 g/mol, preferably in the range of about 20,000 to about 3,000,000 g/mol and more preferably in the range of about 200,000 to about 2,000,000 g/mol.

Ionic hydrophilic polymers include for example polyelectrolytes. Within the context of the invention a polyelectrolyte is understood to be a high molecular weight linear, branched or crosslinked polymer composed of macromolecules comprising constitutional units, in which between 1 and 100% of the constitutional units contain ionized groups when the polyelectrolyte is in the lubricious coating. Herein a constitutional unit is understood to be for example a repeating unit, for example a monomer. A polyelectrolyte herein may refer to one type of polyelectrolyte composed of one type of macromolecules, but it may also refer to two or more different types of polyelectrolytes composed of different types of macromolecules.

For some applications it may be particularly advantageous to use a polyelectrolyte as the hydrophilic polymer, either alone or in combination with a non-ionic hydrophilic polymer, to obtain a more favourable dry-out time. Herein dry-out time is defined as the duration of the lubricious coating remaining lubricious after the device has been taken out of the wetting fluid wherein it has been stored and/or wetted. This is particularly advantageous as a well-recognized problem encountered when using lubricious coatings has been that the coatings may lose water and dry out prior to insertion into the body, or in the body when it comes in contact with e.g. a mucous membrane or vein. Naturally, this affects the lubricity and low-friction properties of the lubricious coating, and may result in complications when the device comprising the lubricious coating is inserted into the body or removed from the body. The dry-out time can be determined by measuring the friction in gram as a function of time the catheter had been exposed to air on the HFT (see above).

Considerations when selecting a suitable polyelectrolyte are its solubility and viscosity in aqueous media, its molecular weight, its charge density, its affinity with the supporting network of the coating and its biocompatibility. Herein biocompatibility means biological compatibility by not producing a toxic, injurious or immunological response in living mammalian tissue.

For a decreased migrateability, the polyelectrolyte is preferably a polymer having a weight average molecular weight of at least about 1000 g/mol, as determinable by light scattering, optionally in combination with size exclusion chromatography. A relatively high molecular weight polyelectrolyte is preferred for increasing the dry-out time and/or reduced migration out of the coating. The weight average molecular weight of the polyelectrolyte is preferably at least 20,000 g/mol, more preferably at least 100,000 g/mol, even more preferably at least about 150,000 g/mol, in particular about 200,000 g/mol or more. For ease of applying the coating it is preferred that the average weight is 1,000,000 g/mol or less, in particular 500,000 g/mol or less, more in particular 300,000 g/mol or less.

Examples of ionized groups that may be present in the polyelectrolyte are ammonium groups, phosphonium groups, sulfonium groups, carboxylate groups, sulfate groups, sulfinic groups, sulfonic groups, phosphate groups, and phosphonic groups. Such groups are very effective in binding water. In one embodiment of the invention the polyelectrolyte also comprises metal ions. Metal ions, when dissolved in water, are complexed with water molecules to form aqua ions $[M(H_2O)_x]^{n+}$, wherein x is the coordination number and n the charge of the metal ion, and are therefore particularly effective in binding water. Metal ions that may be present in the polyelectrolyte are for example alkali metal ions, such as $Na^+$, $Li^+$, or $K^+$, or alkaline earth metal ions, such as $Ca^{2+}$ and $Mg^{2+}$. In particular when the polyelectrolyte comprises quaternary amine salts, for example quaternary ammonium groups, anions may be present. Such anions can for example be halogenides, such as $Cl^-$, $Br^-$, $I^-$ and $F^-$, and also sulphates, nitrates, carbonates and phosphates.

Suitable polyelectrolytes are for example salts of homo- and co-polymers of acrylic acid, salts of homo- and co-polymers of methacrylic acid, salts of homo- and co-polymers of maleic acid, salts of homo- and co-polymers of fumaric acid, salts of homo- and co-polymers of monomers comprising sulfonic acid groups, homo- and co-polymers of monomers comprising quaternary ammonium salts and mixtures and/or derivatives thereof. Examples of suitable polyelectrolytes are poly(acrylamide-co-acrylic acid) salts, for example poly(acrylamide-co-acrylic acid) sodium salt, poly(acrylamide-co-methacrylic acid) salts, for example poly(acrylamide-co-methacrylic acid) sodium salt, poly(methacrylamide-co-acrylic acid) salts, for example poly(methacrylamide-co-acrylic acid) sodium salt, poly(methacrylamide-co-methacrylic acid) salts, for example poly(methacrylamide-co-methacrylic acid) sodium salt poly(acrylic acid) salts, for example poly(acrylic acid) sodium salt, poly(methacrylic acid) salts, for example poly(methacrylic acid) sodium salt, poly(acrylic acid-co-maleic acid) salts, for example poly(acrylic acid-co-maleic acid) sodium salt, poly(methacrylic acid-co-maleic acid) salts, for example poly(methacrylic acid-co-maleic acid) sodium salt, poly(acrylamide-co-maleic acid) salts, for example poly(acrylamide-co-maleic acid) sodium salt, poly(methacrylamide-co-maleic acid) salts, for example poly(methacrylamide-co-maleic acid) sodium salt, poly(acrylamido-2-methyl-1-propanesulfonic acid) salts, poly(4-styrene sulfonic acid) salts, poly(acrylamide-co-dialkyl ammonium chloride), quaternized poly[bis-(2-chloroethyl)ether-alt-1,3-bis[3-(dimethylamino)propyl]urea], polyallylammonium phosphate, poly(diallyldimethylammonium chloride), poly(sodium trimethyleneoxyethylene sulfonate), poly(dimethyldodecyl(2-acrylamidoethyl) ammonium bromide), poly(2-N methylpyridiniumethylene iodine), polyvinylsulfonic acids, and salts of poly(vinyl)pyridines, polyethyleneimines, and polylysines.

Particularly suitable polyelectrolytes are copolymeric polyelectrolytes, which may be random or block copolymers, wherein said copolymeric polyelectrolyte is a copolymer comprising at least two different types of constitutional units, wherein at least one type of constitutional units comprises ionizable or ionized groups and at least one type of constitutional units is absent of ionizable or ionized groups. Herein "ionizable" is understood to be ionizable in neutral aqueous solutions, i.e. solutions having a pH between 6 and 8. An example of such a copolymeric polyelectrolyte is a poly(acrylamide-co-acrylic acid) salt.

In one embodiment of the invention the hydrophilic coating composition comprises a polyelectrolyte. If that is the case, the hydrophilic coating formulation typically comprises 1-90 wt %, 3-50 wt %, 5-30 wt %, or 10-20 wt % of polyelectrolyte based on the total weight of the dry coating.

The non-ionic or ionic hydrophilic polymer may be used in more than 1 wt %, for example more than 10 wt %, more than 20 wt %, or more than 30 weight %, based on the total weight of the dry coating. The hydrophilic polymer can be present up to 95 wt %, however, more often the hydrophilic polymer will be used up to 50, 60, 70 or 80 wt %, based on the total weight of the dry coating.

The hydrophilic coating formulation also comprises a supporting polymer comprising a backbone and at least 2 reactive moieties capable of undergoing polymerization reactions. Herein the supporting polymer may also contain hydrophilic functional groups.

A supporting network can be formed upon curing said supporting polymer. The reactive moiety of the supporting polymer may be selected from the group consisting of radically reactive groups, such as alkenes, amino, amido, sulfhydryl (SH), unsaturated esters, such as acrylate and methacrylate, unsaturated ethers, unsaturated amides, and alkyd/dry resins. The supporting polymer has a backbone and at least one of the above-mentioned reactive moieties. The backbone of the supporting polymer may be selected from the group consisting of polyethers, polyurethanes, polyethylenes, polypropylenes, polyvinyl chlorides, polyepoxides, polyamides, polyacrylamides, poly(meth)acrylics, polyoxazolidones, polyvinyl alcohols, polyethylene imines, polyesters like polyorthoesters and alkyd copolymers, polypeptides, or polysaccharides such as cellulose and starch or any combination of the above. In particular, polymers with unsaturated esters, amides or ethers, thiol or mercaptan groups may suitably be used in the invention.

The supporting polymer has a number average molecular weight in the range of about 750 to about 20,000 g/mol, preferably in the range of about 1,000 to about 15,000 g/mol, more preferably in the range of about 1100 to about 10,000 g/mol, in particular in the range of about 1200 to about 7000 g/mol, more in particular in the range of about 1400 to about 5000 g/mol. The advantage of using a relatively high molecular weight supporting polymer, i.e. having molecular weight of more than about 750 g/mol, preferably more than about 1000 g/mol, is that a relatively open supporting network will be formed. Such a relatively open supporting network will swell more easily and therewith provide the coating with a higher lubricity and a longer dry-out time.

The average number of reactive moieties per molecule of the supporting polymer is preferably in the range of about 1.2 to about 64, more preferably in the range of about 1.2 to about 16, most preferably in the range of about 1.2 to about 8. This means that apart from supporting polymer molecules comprising at least 2 reactive moieties also supporting polymer molecules comprising 1 reactive moiety, i.e. monofunctional polymers, may be present. The monofunctional supporting polymers may also be part of the formed supporting network.

The supporting polymer may be used in more than 1 wt % based on the total weight of the dry coating, for example more than 10%, more than 20 wt %, more than 30 wt % or more than 40 wt %. The supporting polymer can be present in the hydrophilic coating formulation up to 90 wt %, however, more often the supporting polymer will be used up to 50 or 60 wt %, based on the total weight of the dry coating.

In the hydrophilic coating formulation the weight ratio of hydrophilic polymer to supporting polymer may for example vary between 10:90 and 90:10, such as between 25:75 and 75:25 or such as between 60:40 and 40:60.

The invention relates to a hydrophilic coating formulation which when applied to a substrate and cured results in a hydrophilic coating. Herein a hydrophilic coating formulation refers to a liquid hydrophilic coating formulation, e.g. a solution or a dispersion comprising a liquid medium. Herein any liquid medium that allows application of the hydrophilic coating formulation on a surface would suffice. Examples of liquid media are alcohols, like methanol, ethanol, propanol, butanol or respective isomers and aqueous mixtures thereof or acetone, methylethyl ketone, tetrahydrofuran, dichloromethane, toluene, and aqueous mixtures or emulsions thereof or water. The hydrophilic coating formulation further comprises components which when cured are converted into the hydrophilic coating, and thus remain in the hydrophilic coating after curing. Herein curing is understood to refer to physical or chemical hardening or solidifying by any method, for example heating, cooling, drying, crystallization or curing as a result of a chemical reaction, such as radiation-curing or heat-curing. In the cured state all or part of the components in the hydrophilic coating formulation may be crosslinked forming covalent linkages between all or part of the components, for example by using UV or electron beam radiation. However, in the cured state all or part of the components may also be ionically bonded, bonded by dipole-dipole type interactions, or bonded via Van der Waals forces or hydrogen bonds.

The term "to cure" includes any way of treating the formulation such that it forms a firm or solid coating. In particular, the term includes a treatment whereby the hydrophilic polymer further polymerizes, is provided with grafts such that it forms a graft polymer and/or is cross-linked, such that it forms a cross-linked polymer.

The invention also relates to a hydrophilic coating obtainable by applying the hydrophilic coating formulation according to the invention to a substrate and curing it. The invention further relates to a lubricious coating obtainable by applying a wetting fluid to said hydrophilic coating, and to the use of a Norrish Type I and a Norrish Type II photo-initiator in a lubricious coating in order to improve its wear resistance. Further the invention relates to an article, in particular a medical device or a medical device component comprising at least one hydrophilic coating according to the invention and to a method of forming on a substrate the hydrophilic coating according to the invention.

The hydrophilic coating comprises the hydrophilic polymer and a supporting network, which may be a hydrophilic supporting network, and which is formed from the hydrophilic polymer and the supporting polymer. Said hydrophilic coating is formed by curing a hydrophilic coating formulation comprising the hydrophilic polymer, the supporting polymer, the Norrish Type I photoinitiator and the Norrish Type II photoinitiator. Preferably the hydrophilic polymer and/or the hydrophilic supporting network are covalently linked and/or physically bound to each other and/or entrapped to form a polymer network after curing.

The fact that hydrophilic polymer and/or the supporting polymer are covalently and/or physically bound in the hydrophilic coating as part of a polymer network has the advantage that the hydrophilic polymer will hardly leak out into the environment of the hydrophilic coating, for example when it is coated on a medical device. This is particularly useful when the medical device is inside the human or animal body.

In one embodiment of the invention a polyelectrolyte is present in a wetting fluid and introduced into the hydrophilic coating when wetting the hydrophilic coating according to the invention. This is particularly useful for medical devices with a hydrophilic coating which are packed in a fluid, or wherein the hydrophilic coating is wetted in a separate wetting fluid that contains the polyelectrolyte. The invention therefore also relates to coating system for preparing a lubricious coating, said coating system comprising the coating formulation according to the invention and a wetting fluid comprising a polyelectrolyte.

In one embodiment of the invention the hydrophilic coating formulation according to the invention further comprises at least one surfactant, which can improve the surface properties of the coating. Surfactants constitute the most important group of detergent components. Generally, these are water-soluble surface-active agents comprised of a hydrophobic portion, usually a long alkyl chain, attached to hydrophilic or water solubility enhancing functional groups. Surfactants can be categorized according to the charge present in the hydrophilic portion of the molecule (after dissociation in aqueous solution): ionic surfactants, for example anionic or cationic surfactants, and non-ionic surfactants. Examples of ionic surfactants include Sodium dodecylsulfate (SDS), Sodium cholate, Bis(2-ethylhexyl)sulfosuccinate Sodium salt, Cetyltrimethylammoniumbromide (CTAB), Lauryldimethylamine-oxide (LDAO), N-Lauroylsarcosine Sodium salt and Sodium deoxycholate (DOC). Examples of non-ionic surfactants include Alkyl Polyglucosides such as TRITON™ BG-10 Surfactant and TRITON CG-110 Surfactant, Branched Secondary Alcohol Ethoxylates such as TERGI- TOL™ TMN Series, Ethylene Oxide/Propylene Oxide Copolymers, such as TERGITOL L Series, and TERGITOL XD, XH, and XJ Surfactants, Nonylphenol Ethoxylates such as TERGITOL NP Series, Octylphenol Ethoxylates, such as TRITON X Series, Secondary Alcohol Ethoxylates, such as TERGITOL 15-S Series and Specialty Alkoxylates, such as TRITON CA Surfactant, TRITON N-57 Surfactant, TRITON X-207 Surfactant, and Tween, for example Tween 80 or Tween 20.

In the above embodiment typically 0.001 to 1 wt % of surfactant can be applied, preferably 0.05-0.5 wt %, based on the total weight of the dry coating.

In one embodiment of the invention the hydrophilic coating formulation according to the invention further comprises at least one plasticizing agent, which can enhance the flexibility of the coating, which may be preferable when the object to be coated is likely to bend during use. Said plasticizing agent may be included in the hydrophilic coating formulation in a concentration of from about 0.01 wt % to about 15 wt % based on the total weight of the dry coating, preferably from about 1 wt % to about 5.0 wt %. Suitable plasticizers are high boiling compounds, preferably with a boiling point at atmospheric pressure of >200° C., and with a tendency to remain homogeneously dissolved and/or dispersed in the coating after cure. Examples of suitable plasticizers are mono- and polyalcohols and polyethers, such as decanol, glycerol, ethylene glycol, diethylene glycol, polyethylene glycol and/or copolymers with propylene glycol and/or fatty acids.

The invention also relates to a lubricious coating according to the invention having an initial lubricity as measured on a Harland FTS Friction Tester of 20 g or less.

The hydrophilic coating according to the invention can be coated on an article. The hydrophilic coating can be coated on a substrate which may be selected from a range of geometries and materials. The substrate may have a texture, such as porous, non-porous, smooth, rough, even or uneven. The substrate supports the hydrophilic coating on its surface. The hydrophilic coating can be on all areas of the substrate or on selected areas. The hydrophilic coating can be applied to a variety of physical forms, including films, sheets, rods, tubes, molded parts (regular or irregular shape), fibers, fabrics, and particulates. Suitable surfaces for use in the invention are surfaces that provide the desired properties such as porosity, hydrophobicity, hydrophilicity, colorisability, strength, flexibility, permeability, elongation abrasion resistance and tear resistance. Examples of suitable surfaces are for instance surfaces that consist of or comprise metals, plastics, ceramics, glass and/or composites. The hydrophilic coating may be applied directly to the said surfaces or may be applied to a pretreated or coated surface where the pretreatment or coating is designed to aid adhesion of the hydrophilic coating to the substrate.

In one embodiment of the invention the hydrophilic coating according to the invention is coated on a biomedical substrate. A biomedical substrate refers, in part, to the fields of medicine, and the study of living cells and systems. These fields include diagnostic, therapeutic, and experimental human medicine, veterinary medicine, and agriculture. Examples of medical fields include ophthalmology, orthopedics, and prosthetics, immunology, dermatology, pharmacology, and surgery; nonlimiting examples of research fields include cell biology, microbiology, and chemistry. The term "biomedical" also relates to chemicals and compositions of chemicals, regardless of their source, that (i) mediate a biological response in vivo, (ii) are active in an in vitro assay or other model, e.g., an immunological or pharmacological assay, or (iii) can be found within a cell or organism. The term "biomedical" also refers to the separation sciences, such as those involving processes of chromatography, osmosis, reverse osmosis, and filtration. Examples of biomedical articles include research tools, industrial, and consumer applications. Biomedical articles include separation articles, implantable articles, and ophthalmic articles. Ophthalmic articles include soft and hard contact lenses, intraocular lenses, and forceps, retractors, or other surgical tools that contact the eye or surrounding tissue. A preferred biomedical article is a soft contact lens made of a silicon-containing hydrogel polymer that is highly permeable to oxygen. Separation articles include filters, osmosis and reverse osmosis membranes, and dialysis membranes, as well as bio-surfaces such as artificial skins or other membranes. Implantable articles include catheters, and segments of artificial bone, joints, or cartilage. An article may be in more than one category, for example, an artificial skin is a porous, biomedical article. Examples of cell culture articles are glass beakers, plastic petri dishes, and other implements used in tissue cell culture or cell culture processes. A preferred example of a cell culture article is a bioreactor micro-carrier, a silicone polymer matrix used in immobilized cell bioreactors, where the geometry, porosity, and density of the particulate micro-carrier may be controlled to optimize performance. Ideally, the micro-carrier is resistant to chemical or biological degradation, to high impact stress, to mechanical stress (stirring), and to repeated steam or chemical sterilization. In addition to silicone polymers, other materials may also be suitable. This invention may also be applied in the food industry, the paper printing industry, hospital supplies, diapers and other liners, and other areas where hydrophilic, wettable, or wicking articles are desired.

The medical device can be an implantable device or an extracorporeal device. The devices can be of short-term temporary use or of long-term permanent implantation. In certain embodiments, suitable devices are those that are typically used to provide for medical therapy and/or diagnostics in heart rhythm disorders, heart failure, valve disease, vascular disease, diabetes, neurological diseases and disorders, orthopedics, neurosurgery, oncology, ophthalmology, and ENT surgery.

Suitable examples of medical devices include, but are not limited to, a stent, stent graft, anastomotic connector, synthetic patch, lead, electrode, needle, guide wire, catheter, sensor, surgical instrument, angioplasty balloon, wound drain, shunt, tubing, infusion sleeve, urethral insert, pellet, implant, blood oxygenator, pump, vascular graft, vascular access port, heart valve, annuloplasty ring, suture, surgical clip, surgical staple, pacemaker, implantable defibrillator, neurostimulator, orthopedic device, cerebrospinal fluid shunt, implantable drug pump, spinal cage, artificial disc, replacement device for nucleus pulposus, ear tube, intraocular lens and any tubing used in minimally invasive surgery.

Articles that are particularly suited to be used in the present invention include medical devices or components such as catheters, for example intermittent catheters, balloon catheters, PTCA catheters, stent delivery catheters, guide wires, stents, syringes, metal and plastic implants, contact lenses and medical tubing.

The hydrophilic coating formulation can be applied to the substrate by for example dip-coating. Other methods of application include spray, wash, vapor deposition, brush, roller and other methods known in the art.

The thickness of the hydrophilic coating according to the invention may be controlled by altering the soaking time, drawing speed, viscosity of the hydrophilic coating formulation, the number of coating steps and the solids content. Typically the thickness of a hydrophilic coating on a substrate ranges from 0.1-300 µm, preferably 0.5-100 µm, more preferably 1-30 µm. If a polyelectrolyte is present in the hydrophilic coating composition the concentration of ionic or ionizable groups may further be controlled by altering the type of polyelectrolyte or the polyelectrolyte concentration in the hydrophilic coating formulation.

The invention further relates to a method of forming on a substrate a hydrophilic coating which has a low coefficient of friction when wetted with a water-based liquid, the method comprising applying a hydrophilic coating formulation according to the invention to at least one surface of the article and allowing the hydrophilic coating formulation to cure by exposing the formulation to electromagnetic radiation thereby activating the initiator.

To apply the hydrophilic coating on the substrate, a primer coating may be used in order to provide a binding between the hydrophilic coating and the substrate. The primer coating is often referred to as the primary coating, base coat or tie coat. Said primer coating is a coating that facilitates adhesion of the hydrophilic coating to a given substrate, as is described in for example WO02/10059. The binding between the primer coating and the hydrophilic coating may occur due to covalent or ionic links, hydrogen bonding, physisorption or polymer entanglements. These primer coatings may be solvent based, water based (latexes or emulsions) or solvent free and may comprise linear, branched and/or crosslinked components. Typical primer coatings that could be used comprise for example polyether sulfones, polyurethanes, polyesters, including polyacrylates, as described in for example U.S. Pat. No. 6,287,285, polyamides, polyethers, polyolefins and copolymers of the mentioned polymers.

In particular, the primer coating comprises a supporting polymer network, the supporting network optionally comprising a functional hydrophilic polymer entangled in the supporting polymer network as described in WO2006/056482 A1. The information with respect to the formulation of the primer coating is herewith incorporated by reference.

A primer layer as described above is in particular useful for improving adherence of a coating comprising a hydrophilic polymer such as a polylactam, in particular PVP and/or another of the above identified hydrophilic polymers, in particular on polyvinylchloride (PVC), silicone, polyamide, polyester, polyolefin, such as polyethylene, polypropylene and ethylene-propylene rubber (e.g. EPDM), or a surface having about the same or a lower hydrophilicity. In general there is no restriction as to the thickness of the primer layer, but typically the thickness is less than 5 µm, less than 2 µm or less than 1 µm.

In an embodiment, the surface of the article is subjected to oxidative, photo-oxidative and/or polarizing surface treatment, for example plasma and/or corona treatment in order to improve the adherence of the coating which is to be provided. Suitable conditions are known in the art.

Application of the formulation of the invention may be done in any manner. Curing conditions can be determined, based on known curing conditions for the photo-initiator and polymer or routinely be determined.

In general, curing may be carried out at any suitable temperature depending on the substrate, as long as the mechanical properties or another property of the article are not adversely affected to an unacceptable extent.

Intensity and wavelength of the electromagnetic radiation can routinely be chosen based on the photoinitiator of choice. In particular, a suitable wavelength in the UV, visible or IR part of the spectrum may be used.

The invention will be further illustrated by the following examples.

EXAMPLES

A primer coating formulation was prepared as indicated below.

Primer Coating Formulation (used in Examples 1-3 and Comparative Example A)

| | |
|---|---|
| PTGL1000(T-H)$_2$* | 5.00% (w/w) |
| Irgacure 2959 (Aldrich) | 0.20% (w/w) |
| Ethanol (Merck, 96%, extra pure PH EUR, BP) | 94.8% (w/w) |

*synthesized as described below

The above mentioned components were added to a brown colored glass flask and mixed overnight (~16 hours) at room temperature. The next morning the primer formulation had become a homogeneous liquid with a viscosity of 6 mPa·s. Herein the viscosity was measured on a Brookfield CAP1000, v.1.2 in combination with cone nr. 1 at 25° C.

The above primer coating formulation was applied to a polyurethane-jacketed Nitinol wire with an outer diameter of 0.031" (0.79 mm) using a Harland 175-24 PCX coater. The application parameters are listed in Table 1.

TABLE 1

Application conditions of the primer coating formulation

| | |
|---|---|
| Solids primer [w/w %] | 5 |
| Viscosity [mPa · s] | 6 |
| Draw speed primer [cm/s] | 4 |
| Cure time primer [s] | 15 |

Synthesis of PTGL1000(T-H)$_2$

In a dry inert atmosphere toluene diisocyanate (TDI or T, Aldrich, 95% purity, 87.1 g, 0.5 mol), Irganox 1035 (Ciba Specialty Chemicals, 0.58 g, 1 wt % relative to hydroxy ethyl acrylate (HEA or H)) and tin(II) 2-ethyl hexanoate (Sigma, 95% purity, 0.2 g, 0.5 mol) were placed in a 1 liter flask and stirred for 30 minutes. The reaction mixture was cooled to 0° C. using an ice bath. HEA (Aldrich, 96% purity, 58.1 g, 0.5 mol) was added dropwise in 30 min, after which the ice bath was removed and the mixture was allowed to warm up to room temperature. After 3 h the reaction was complete. Poly (2-methyl-1,4-butanediol)-alt-poly(tetramethyleneglycol) (PTGL1000, Hodogaya, M$_n$=1000 g/mol, 250 g, 0.25 mol) was added dropwise in 30 min.

Subsequently the reaction mixture was heated to 60° C. and stirred for 18 h, upon which the reaction was complete as indicated by GPC (showing complete consumption of HEA), IR (displayed no NCO related bands) and NCO titration (NCO content below 0.02 wt %).

Examples 1-3

Three hydrophilic coating formulations (Examples 1-3) were prepared, all comprising a Norrish Type I (Irgacure 2959) and a Norrish Type II (benzophenone) photoinitiator. Relative to the total solids content, the hydrophilic coating formulation of Example 2 comprised twice as much benzophenone compared to the hydrophilic coating formulation of Example 1. The hydrophilic coating formulation of Example 3 had a higher total solids content than the hydrophilic coating formulations of Examples 1 and 2, i.e. 8 wt % vs. 4 wt %. Relative to the total solids content the hydrophilic coating formulations of Example 2 and Example 3 comprised the same amount of benzophenone.

Hydrophilic Coating Formulations of Example 1-3

|  | Example 1 | Example 2 | Example 3 |
|---|---|---|---|
| PEG4000DA* | 2.00 wt % | 2.00 wt % | 4.00 wt % |
| Polyvinylpyrollidone (PVP, 1.3M, Aldrich) | 2.00 wt % | 2.00 wt % | 4.00 wt % |
| Benzophenone (Aldrich) | 0.08 wt % | 0.16 wt % | 0.32 wt % |
| Irgacure 2959 | 0.04 wt % | 0.04 wt % | 0.08 wt % |
| Tween 80 (surfactant, Merck) | 0.04 wt % | 0.04 wt % | 0.08 wt % |
| Distilled water | 47.92 wt % | 47.88 wt % | 45.76 wt % |
| MeOH (Merck pa) | 47.92 wt % | 47.88 wt % | 45.76 wt % |

*synthesized as described below

The above mentioned components were added to brown colored glass flasks and mixed overnight (~16 hours) at room temperature. The next morning the hydrophilic coating formulations had become homogeneous liquids with viscosities as indicated in Table 2. Herein the viscosity was measured on a Brookfield CAP1000, v.1.2 in combination with cone nr. 1 at 25° C.

Comparative Experiment A

For comparison hydrophilic coating formulation A was prepared without Norrish Type II photoinitiator.

Hydrophilic Coating Formulation of Comparative Experiment A

| PEG4000DA* | 2.00 wt % |
|---|---|
| PVP 1.3M | 2.00 wt % |
| Benzophenone | — |
| Irgacure 2959 | 0.04 wt % |
| Tween 80 | 0.04 wt % |
| Water | 47.96 wt % |
| MeOH | 47.96 wt % |

*synthesized as described below

The above mentioned components were added to a brown colored glass flask and mixed overnight (~16 hours) at room temperature. The next morning the hydrophilic coating formulation had become a homogeneous liquid with a viscosity as indicated in Table 2. Herein the viscosity was measured on a Brookfield CAP1000, v.1.2 in combination with cone nr. 1 at 25° C.

Synthesis of PEG4000DA 150 g (75 mmol OH) of polyethyleneglycol (PEG4000, Biochemika Ultra from Fluka, Ohio value 28.02 mg KOH/g, 499.5 mew/kg, $M_n$=4004 g/mol) was dissolved in 350 ml of dry toluene at 45° C. under nitrogen atmosphere. 0.2 g (0.15 wt %) of Irganox 1035 was added as a radical stabilizer. The resulting solution was distilled azeotropically overnight (50° C., 70 mbar) leading the condensed toluene over 4 Å mol sieves. For each batch of PEG the OH value was accurately determined by OH titration, which was performed according to the method described in the 4th edition of the European Pharmacopoeia, paragraph 2.5.3, Hydroxyl Value, page 105.

This made it possible to calculate the amount of acryloyl chloride to be added and to determine the degree of acrylate esterification during the reaction. 9.1 g (90 mmol) of triethylamine was added to the reaction mixture, followed by a dropwise addition of 8.15 g (90 mmol) of acryloyl chloride dissolved in 50 ml of toluene in 1 h. Triethylamine and acryloyl chloride were colorless liquids. The reaction mixture was stirred for 2 to 4 h at 45° C. under nitrogen atmosphere. During the reaction the temperature was kept at 45° C. to prevent crystallization of PEG. To determine the conversion a sample was withdrawn from the reaction mixture, dried and dissolved in deuterated chloroform. Trifluoro acetic anhydride (TFAA) was added and a $^1$H-NMR spectrum was recorded. TFAA reacts with any remaining hydroxyl groups to form a trifluoro acetic ester, which can be easily detected using $^1$H-NMR spectroscopy (the triplet signal of the methylene protons in the α-position of the trifluoro acetic acid group (g, 4.45 ppm) can be clearly distinguished from the signal of the methylene groups in the α-position of the acrylate ester (d, 4.3 ppm)). At a degree of acrylate esterification less than 98% an additional 10 mmol of acryloyl chloride and triethylamine were added to the reaction mixture allowing it to react for 1 h. At a degree of acrylate esterification >98% the warm solution was filtered to remove triethylamine hydrochloride salts.

Approximately 300 ml of toluene was removed under vacuum (50° C., 20 mbar). The remaining solution was kept at 45° C. in a heated dropping funnel and added dropwise to 1 liter of diethyl ether (cooled in an ice bath). The ether suspension was cooled for 1 h before the PEG diacrylate product was obtained by filtration. The product was dried overnight at room temperature under reduced air atmosphere (300 mbar). Yield: 80-90% as white crystals.

Hydrophilic coating formulations 1, 2, A and 3 were applied to the polyurethane-jacketed Nitinol wire with primer coating using a Harland 175-24 PCX coater. For each primer coating-hydrophilic coating combination three different draw speeds were used to vary the coating thickness. Hydrophilic coating formulation 3 comprised 8 wt % solids which further increases the coating thickness. The relevant application conditions used are represented in Table 2.

TABLE 2

Application conditions for hydrophilic coating formulations 1, 2, A and 3

|  | 1 | 2 | A | 3 |
|---|---|---|---|---|
| Solids topcoat [wt %] | 4 | 4 | 4 | 8 |
| Viscosity [mPa · s] | 15 | 17 | 18 | 35 |
| Draw speed topcoat [cm/s] | 4 | 4 | 4 | 2 |
| Cure time topcoat [s] | 360 | 360 | 360 | 360 |

The coated length of the polyurethane-jacketed Nitinol wires was 80 cm for the primer coating and the hydrophilic coatings. On average the UV light intensity in the PCX coater is 60 mW/cm$^2$ between 250-400 nm, measured with a Harland UVR335 (IL1400) light meter in combination with detector SED005#989 and filter WBS320#27794. The primer coating was exposed to UV light for 15 seconds, while the hydrophilic coating was exposed for 360 seconds, corresponding to a UV-dose of 0.9 J/cm$^2$ and 21.6 J/cm$^2$, respectively. For applied coating parameters see Table 3.

TABLE 3

Applied process parameters in PCX coater
Harland Coating parameters selection table

|  | Primer | Hydrophilic coating | Units |
|---|---|---|---|
| Dipping Cycle |  |  |  |
| 1) Select funnel set | 1 | 2 |  |
| 2) Move device carrier to position | 160 | 160 | Cm |
| Speed | 6.5 | 6.5 | Cm/sec |
| acceleration time | 0.1 | 0.1 | Sec |

TABLE 3-continued

Applied process parameters in PCX coater
Harland Coating parameters selection table

| | Primer | Hydrophilic coating | Units |
|---|---|---|---|
| 3) Operator Prompt | "Place devices in the carrier and clean them with ethanol" | | |
| 4) Operator Prompt | "Take the wires out of the carrier and put them manually in the solution tubes" | | |
| 5) Move device carrier to position | 2.1 | 2.1 | Cm |
| Speed | 6.5 | 6.5 | Cm/sec |
| acceleration time | 0.1 | 0.1 | Sec |
| 6) Operator Prompt | "Attach the wires to the device carrier" | | |
| 7) Time Pause | 10 | 10 | Sec |
| 8) Move device carrier up | 83 | 83 | |
| Speed | 4.0 | 4.0 or 2.0 | Cm/sec |
| acceleration time | 0.1 | 0.1 | Sec |
| 9) Move device carrier to position | 174 | 174 | Cm |
| Speed | 6.5 | 6.5 | Cm/sec |
| acceleration time | 0.1 | 0.1 | Sec |
| 10) Operator Prompt | "Close doors" | | |
| Cure Cycle | | | |
| 1) Rotator On | 4 | 4 | Rpm |
| 2) UV lights Full Power | A-D and H-K | | |
| 3) Open shutter | | | |
| 4) Time pause | 15 | 360 | Sec |
| 5) Close Shutter | | | |
| 6) UV lights Standby Power | A-D and H-K | | |
| 7) Rotator Off | | | |

Lubricity Tests:

The coated polyurethane-jacketed Nitinol wires were subjected to lubricity tests which were performed on the Harland Friction Tester FTS5000 (HFT). The friction in the HFT was measured against Shore A 60 durometer silicone pads emersed in demineralized water. Test conditions are listed in Table 4.

TABLE 4

Harland friction tester test conditions

| Transport movement (cm) | 10 |
|---|---|
| Clamp force (g) | 300 |
| Pull speed (cm/s) | 1 |
| Acceleration time (s) | 2 |
| Runs | 25 |
| Pads cleaned between runs | No |

After testing the samples in the HFT the coated Nitinol wires were subjected to a more severe test by manually rubbing the samples with a compress gauze (Johnson & Johnson, gauze pad, 4×4", order no. 53053). The samples as well as the gauze pads were soaked in demineralized water prior to the rub test. The excess of water was gently squeezed out of the gauze pad and the gauze was wrapped around the sample. The sample and gauze were firmly pressed between index-finger and thumb and the gauze was pulled downwards along the sample of a length of 20 cm. This sequence was repeated 24 times (25 rubs in total).

After the gauze rubs the samples were placed back into the HFT and a second test as described in Table 4 was performed on the parts of the samples exposed to gauze rubs.

The test results are given in Tables 5, 6, 7 and 8 for hydrophilic coatings 1, 2, A, and 3 respectively. The friction force after the gauze rub test compared to the friction force before the gauze rub test is a measure of the remaining lubricity (better if it remains low) and as such a measure for the wear resistance under severe test conditions.

TABLE 5

Friction force in HFT of hydrophilic coating 1 applied before and after the gauze rub test.

| Friction in HFT [g] | |
|---|---|
| 1st cycle before gauze rubs | 4.4 |
| 25th cycle before gauze rubs | 4.5 |
| 1st cycle after 25 gauze rubs | 13.1 |
| 25th cycle after 25 gauze rubs | 51.7 |

TABLE 6

Friction force in HFT of hydrophilic coating 2 applied before and after the gauze rub test.

| Friction in HFT [g] | |
|---|---|
| 1st cycle before gauze rubs | 9 |
| 25th cycle before gauze rubs | 9.2 |
| 1st cycle after 25 gauze rubs | 9.7 |
| 25th cycle after 25 gauze rubs | 16.5 |

TABLE 7

Friction force in HFT of hydrophilic coating A applied before and after the gauze rub test.

| Friction in HFT [g] | |
|---|---|
| 1st cycle before gauze rubs | 3.3 |
| 25th cycle before gauze rubs | 3.8 |
| 1st cycle after 25 gauze rubs | 28.8 |
| 25th cycle after 25 gauze rubs | >100 |

From the above results for hydrophilic coating 1 (Example 1), hydrophilic coating 2 (Example 2) and hydrophilic coating A (Comparative Experiment A) it can be concluded that hydrophilic coating A (without the Norrish Type II photoinitiator) exhibits a significantly lower wear resistance than hydrophilic coatings 1 and 2 (with the Norrish Type II photoinitiator). For hydrophilic coating A the friction in the HFT after the gauze rub test becomes very high and increases rapidly with multiple cycles in the HFT, while the friction after the gauze test for hydrophilic coating 1 and in particular hydrophilic coating 2 (higher benzophenone content) is still at an acceptable level.

In Table 8 the result for hydrophilic coating 3 is given, which is a thicker coating (due to the higher solids content of the hydrophilic coating formulation).

TABLE 8

Friction force in HFT of hydrophilic coating 3 applied before and after the gauze rub test.

| Friction in HFT [g] | |
|---|---|
| 1st cycle before gauze rubs | 5.8 |
| 25th cycle before gauze rubs | 5.9 |
| 1st cycle after 25 gauze rubs | 10.3 |
| 25th cycle after 25 gauze rubs | 10.0 |

A comparison of the results of hydrophilic coating 3 with those of hydrophilic coating 2 (same benzophenone content based on solids) shows that thicker coatings obtained from a hydrophilic coating formulation comprising benzophenone provide an even higher wear resistance.

The invention claimed is:

1. A coating formulation for preparing a hydrophilic coating,
   wherein the hydrophilic coating formulation comprises:
   (a) a hydrophilic polymer;
   (b) a supporting polymer comprising a backbone and at least 2 reactive moieties capable of undergoing polymerization reactions, wherein the supporting polymer has a number average molecular weight in the range of 1,100-10,000 g/mol;
   (c) a Norrish Type I photoinitiator; and
   (d) a Norrish Type II photoinitiator, wherein
   a weight ratio of the Norrish Type I photoinitiator to the Norrish Type II photoinitiator is between 5:1 and 1:5.

2. The coating formulation according to claim 1, wherein the Norrish Type I photoinitiator is chosen from the group consisting of benzoin derivatives, methylolbenzoin derivatives, 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, and halogenated acetophenone derivatives.

3. The coating formulation according to claim 1, wherein the Norrish Type II photoinitiator is chosen from the group consisting of benzophenone, xanthone, derivatives of benzophenone, blends of benzophenone and benzophenone derivatives, Michler's Ketone, Ethyl Michler's Ketone, thioxanthone, xanthone derivatives, benzil, anthraquinones, coumarin, and derivatives and mixtures thereof.

4. The coating formulation according to claim 1, wherein the total amount of photoinitiator in the coating formulation is between 0.2 and 10 wt %, based on the total weight of the dry coating.

5. The coating formulation according to claim 1, wherein the hydrophilic polymer is a non-ionic hydrophilic polymer selected from the group consisting of poly(lactams), polyurethanes, homo- and copolymers of acrylic and methacrylic acid, polyvinyl alcohol, polyvinylethers, maleic anhydride copolymers, vinylamines, polyethyleneimines, polyethyleneoxides, polypropyleneoxides, poly(carboxylic acids), polyamides, polyanhydrides, polyphosphazenes, methyl cellulose, carboxymethyl cellulose, hydroxymethyl cellulose, and hydroxypropylcellulose, heparin, dextran, polypeptides, polysachamides, and polyesters.

6. The coating formulation according to claim 1, wherein the hydrophilic polymer is a polyelectrolyte selected from the group consisting of homo- and co-polymers of acrylic acid, salts of homo- and co-polymers of methacrylic acid, salts of homo- and co-polymers of maleic acid, salts of homo- and co-polymers of fumaric acid, salts of homo- and co-polymers of monomers comprising sulfonic acid groups, homo- and co-polymers of monomers comprising quarternary ammonium salts, derivatives and mixtures thereof.

7. The coating formulation according to claim 1, comprising both a non-ionic polymer and a polyelectrolyte, wherein the non-ionic polymer is selected from the group consisting of poly(lactams), polyurethanes, homo- and copolymers of acrylic and methacrylic acid, polyvinyl alcohol, polyvinylethers, maleic anhydride based copolymers, vinylamines, polyethyleneimines, polyethyleneoxides, polypropyleneoxides, poly(carboxylic acids), polyamides, polyanhydrides, polyphosphazenes, cellulosics, heparin, dextran, polypeptides, polysachamides, and polyesters and wherein the polyelectrolyte is selected from the group consisting of homo- and co-polymers of acrylic acid, salts of homo- and co-polymers of methacrylic acid, salts of homo- and co-polymers of maleic acid, salts of homo- and co-polymers of fumaric acid, salts of homo- and co-polymers of monomers comprising sulfonic acid groups, homo- and co-polymers of monomers comprising quarternary ammonium salts, derivatives and mixtures thereof.

8. The coating formulation according to claim 1 wherein the backbone of the supporting polymer is selected from the group consisting of polyethers, polythioethers, polyurethanes, polyethylenes, polypropylenes, polyvinyl chlorides, polyepoxides, polyamides, polyacrylamides, poly(meth)acrylics, polyoxazolidones, polyvinyl alcohols, polyethylene imines, polyesters, polypeptides, polysaccharides, and combinations thereof, and wherein the at least 2 reactive moieties are selected from the group consisting of alkenes, amino, amido, sulfhydryl (SH), unsaturated esters, unsaturated ethers, and unsaturated amides.

9. A hydrophilic coating obtained by applying a coating formulation according to claim 1 onto a substrate, and curing the coating formulation.

10. A lubricious coating obtained by applying a wetting fluid to a hydrophilic coating according to claim 9.

11. The lubricious coating according to claim 10 having an initial lubricity after 1 cycle as measured on a Harland FTS Friction Tester of 20 g or less.

12. The lubricious coating according to claim 10 having a wear resistance, as measured on a Harland FTS Friction Tester after 25 gauze rubs, is 60 g or less at a clamp force of 300 g.

13. A coating system for preparing a lubricious coating, said coating system comprising a coating formulation according to claim 1 and a wetting fluid comprising a polyelectrolyte.

14. An article comprising at least one hydrophilic coating according to claim 9.

15. The article according to claim 14, wherein the article is a medical device or component.

16. The article according to claim 15, wherein the medical device or component comprises a catheter, a medical tubing, a guide wire, a stent, or a membrane.

17. A method of forming on a substrate a hydrophilic coating, the method comprising
   applying a coating formulation according to claim 1 to at least one surface of an article; and
   allowing the coating formulation to cure by exposing the coating formulation to electromagnetic radiation thereby activating the initiator.

18. The coating formulation of claim 1, wherein the supporting polymer has a number average molecular weight in the range 1,200-7,000 g/mol.

19. The coating formulation of claim 1, wherein the supporting polymer has a number average molecular weight in the range 1,400-5,000 g/mol.

* * * * *